(12) United States Patent  
Rosenman

(10) Patent No.: US 6,726,654 B2
(45) Date of Patent: Apr. 27, 2004

(54) SYSTEM AND METHOD FOR DELIVERING THERMALLY SENSITIVE AND REVERSE-THERMAL GELATION MATERIALS

(75) Inventor: Daniel C. Rosenman, South San Francisco, CA (US)

(73) Assignee: BioCardia, Inc., South San Francisco, CA (US)

( * ) Notice: Subject to any disclaimer, the term of this patent is extended or adjusted under 35 U.S.C. 154(b) by 0 days.

(21) Appl. No.: 10/308,344

(22) Filed: Dec. 2, 2002

(65) Prior Publication Data

US 2003/0125665 A1 Jul. 3, 2003

Related U.S. Application Data

(63) Continuation of application No. 09/632,865, filed on Aug. 4, 2000, now Pat. No. 6,488,659.
(60) Provisional application No. 60/147,523, filed on Aug. 5, 1999.

(51) Int. Cl.$^7$ .................................................. A61F 7/12
(52) U.S. Cl. ............................. 604/113; 606/22; 606/27
(58) Field of Search ................................ 604/113, 264; 606/21, 22, 23, 24, 25, 27, 28

(56) References Cited

U.S. PATENT DOCUMENTS

| | | | |
|---|---|---|---|
| 4,474,752 A | 10/1984 | Haslam et al. ................ 424/78 |
| 4,478,822 A | 10/1984 | Haslam et al. ................ 424/78 |
| 4,508,123 A | 4/1985 | Wyatt et al. ................ 128/692 |
| 5,108,372 A | 4/1992 | Swenson .................... 604/113 |
| 5,124,151 A | 6/1992 | Viegas et al. ............... 424/422 |
| 5,190,539 A | 3/1993 | Fletcher et al. ............... 606/25 |
| 5,195,976 A | 3/1993 | Swenson .................... 604/113 |
| 5,211,631 A * | 5/1993 | Sheaff ........................ 604/113 |
| 5,306,501 A | 4/1994 | Viegas et al. ............... 424/423 |
| 5,330,768 A | 7/1994 | Park et al. ................... 424/501 |
| 5,624,392 A | 4/1997 | Saab ........................... 604/43 |
| 5,653,692 A * | 8/1997 | Masterson et al. ........... 604/113 |
| 5,702,717 A | 12/1997 | Cha et al. .................... 424/425 |
| 5,728,066 A * | 3/1998 | Daneshvar .................... 604/96 |
| 5,741,248 A * | 4/1998 | Stern et al. .................... 606/21 |
| 5,833,685 A | 11/1998 | Tortal et al. .................... 606/23 |
| 5,891,094 A * | 4/1999 | Masterson et al. ........... 604/113 |
| 5,902,268 A | 5/1999 | Saab ........................... 604/43 |
| 5,989,238 A * | 11/1999 | Ginsburg ..................... 604/500 |
| 6,042,559 A * | 3/2000 | Dobak, III ...................... 604/7 |
| 6,165,164 A | 12/2000 | Hill et al. ..................... 604/523 |
| 6,231,595 B1 * | 5/2001 | Dobak, III ................... 607/106 |
| 6,242,472 B1 * | 6/2001 | Sekins et al. ................ 514/396 |
| 6,270,476 B1 | 8/2001 | Santaianni et al. ....... 604/95.04 |
| 6,290,696 B1 | 9/2001 | Lafontaine ................... 606/21 |
| 6,350,276 B1 | 2/2002 | Knowlton .................... 607/104 |

* cited by examiner

*Primary Examiner*—Marc Norman
(74) *Attorney, Agent, or Firm*—K. David Crockett, Esq.; Crockett & Crockett

(57) ABSTRACT

A catheter for injecting a thermally sensitive gelation material to remote sites within a patient's body by maintaining the thermally sensitive gelation material in a liquid state until it is delivered to a target area within the body.

38 Claims, 6 Drawing Sheets

SYSTEM AND METHOD FOR DELIVERING THERMALLY SENSITIVE AND REVERSE-THERMAL GELATION MATERIALS

RELATED PATENT APPLICATION

This application is a continuation of U.S. application Ser. No. 09/632,865, filed Aug. 4, 2000, now U.S. Pat. No. 6,448,659, which claimed priority to provisional application 60/147,523 filed Aug. 5, 1999.

FIELD OF THE INVENTION

This application relates generally to catheters, and more specifically to catheters and methods for delivering thermally sensitive gelation materials and reverse-thermal gelation materials to remote sites in the body.

BACKGROUND OF THE INVENTIONS

In many disease states, doctors want to deliver a therapeutic agent to a target area and have the agent remain in the target area to treat the tissue for an extended period of time. If the therapeutic agent has the consistency of liquid, the body quickly and efficiently carries it away from the target area. As a result, the duration of time that the agent has to treat the target area is short.

In order to reduce the body's ability to carry the therapeutic agent away from the target area others have increased the viscosity of the therapeutic agent such that it has the consistency of gel. Using gels is effective because the diffusion rates of gels are slower than the diffusion rates of liquids. Thus the gel elutes the therapeutic agent over a longer time course treating the target area for a greater period of time. There are many types of gels that can incorporate therapeutic agents. Each type of gel changes viscosity in response to different environments. Those environments include pH, temperature, catalyst, chemical reaction, solvent, or reaction with compounds in the body.

Catheters are traditionally used to deliver therapeutic agents to remote target areas in the body. Generally catheters traverse the vascular pathways of the body until the tip of the catheter reaches the target area. Catheters are used in the cardiovascular, gastric, general, urological, neurological, and oncological fields of medicine. The target area can be a blood vessel, an organ, or a tumor. Catheters have been used to deliver acute therapeutic agents such as analgesic, antibacterial, anti-restenotic, anticancer, anti-inflammatory agents and hormones, and bulking agents such as collagen and stainless steel micro-embolic coils. However, due to the small size and long length of the catheters they cannot deliver viscous materials such as gels to remote sites in the body.

One way to circumvent the problem of delivering viscous materials is to use a special class of gels, known as reverse-thermal gelation gels (also known by the trademarked name PLURONIC® gels or TETRONIC® gels, available from BASF and other suppliers). These gels are characterized by the property of being liquid below a critical solution temperature and becoming viscous, or gel-like, above the critical solution temperature. This is in contrast with normal matter that is solid below a critical temperature, for example, the freezing temperature and liquid above that critical temperature, exhibiting decreased viscosity as the temperature of the matter increases. The critical solution temperature of these gels can be tailored by their chemistry such that they are liquid at room temperature or below (0–23° C.) and gel at body temperature (37° C.).

There have been many studies of the biological behavior of sustained release of substances from PLURONIC® gels in animals. This gel has typically been delivered to shallow tissue in animals through a syringe. It is possible to deliver it in this manner because the delivery path is short enough that the liquid doesn't gel before it is delivered through the syringe tip because the animal's body heat does not have sufficient time to heat it up.

Gels, however, cannot be delivered to remote sites in the body such as the heart or the brain through a catheter because the gels are too viscous to be injected.

SUMMARY OF THE INVENTION

The devices and methods claimed below allow thermally sensitive gelation materials to be injected into remote sites within a patient's body.

The injection catheter includes a hollow needle, a catheter body, a handle, and a syringe. The syringe is located at the proximal end of the injection catheter and the hollow needle is located at the distal end.

One embodiment includes a thermally insulated injection catheter that has an insulated catheter body. The insulated catheter body includes a catheter wall, a stainless steel mesh layer, an insulation layer, and a solution tube. The catheter body can also include second tube, called the alternate tube, which extends from the distal to the proximal end of the catheter. This alternate tube joins the solution tube at a Y-junction proximate to the hollow needle.

Another embodiment includes a catheter body having a catheter wall, a solution tube, an input tube and an output tube. The input tube surrounds the solution tube and carries a fluid, gas or liquid, along the length of the solution tube for maintaining the therapeutic solution in a liquid state.

A further embodiment combines cooling fluid and reverse-thermal solution into one tube by injecting reverse-thermal solution "plugs" separated and carried by the cooling fluid. The plugs move down the tube, pushed by the force of injected saline. Once the discrete plugs are lodged in the target area, the saline would be transported away by the body, leaving the reverse-thermal solution plug in place to harden and elute its therapeutic agent over time.

In another embodiment, therapeutic solution is in a reservoir located at the distal end of the catheter. The therapeutic solution is liquefied at a neck section, which is located proximate to the hollow needle that delivers the therapeutic solution. The input tube coils around the neck section and the fluid flows, in the direction of the arrow D, through the input tube liquefying the therapeutic solution, then out the output tube.

DETAILED DESCRIPTION

The devices and methods described below provide for the delivery of controlled-release therapeutic agents to distant locations in the body through small access areas.

A therapeutic solution is a thermally sensitive gelling material combined with a therapeutic agent. The term "thermally sensitive gelling material" includes both normal thermal gels and reverse-thermal gels. A thermal gel that works in a patient's body must gel at body temperature and be a liquid at a temperature higher than body temperature. Examples of such materials are collagen and PLA/PLG copolymers. As discussed above, PLURONIC® gel is a reverse-thermal gel that can be used in a patients body.

A thermal solution is a combination of a normal thermal gel and a therapeutic agent, and a reverse-thermal solution is a combination of a reverse-thermal gel and a therapeutic agent. The term "solution" is used in its broad sense, and is meant to encompass a solution, a suspension, and any other form of combining a gel with a therapeutic agent.

Figure 1:
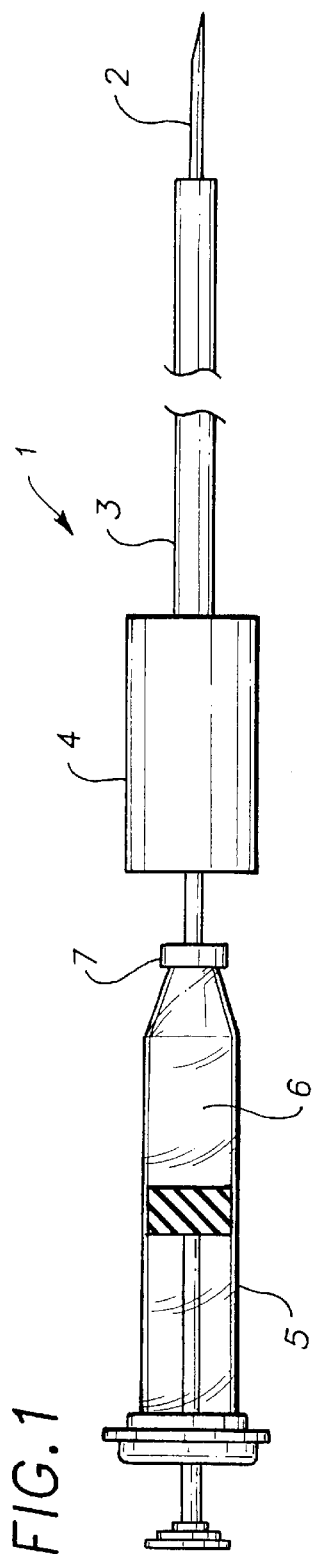
FIG. 1 is an isometric view of an injection catheter.

FIG. 1 illustrates an injection catheter 1. The injection catheter includes a hollow needle 2, a catheter body 3, a handle 4, and a syringe 5. The syringe is located at the proximal end of the injection catheter and the hollow needle is located at the distal end. The term hollow needle is meant to encompass any hollow puncturing element. The hollow needle is typically a 27 or 28-gauge needle that is in fluid communication with the syringe. The syringe provides the force for moving the therapeutic solution through the catheter body.

The syringe 5 is coupled to the catheter body 3 through a first luer 7 that can be fixed or rotating hemostatic type. The handle 4 advances the catheter body and optionally transmits torque to the catheter body. The catheter body carries the therapeutic solution from the syringe, or other injection device, to a target area within the patient's body.

Figure 2:
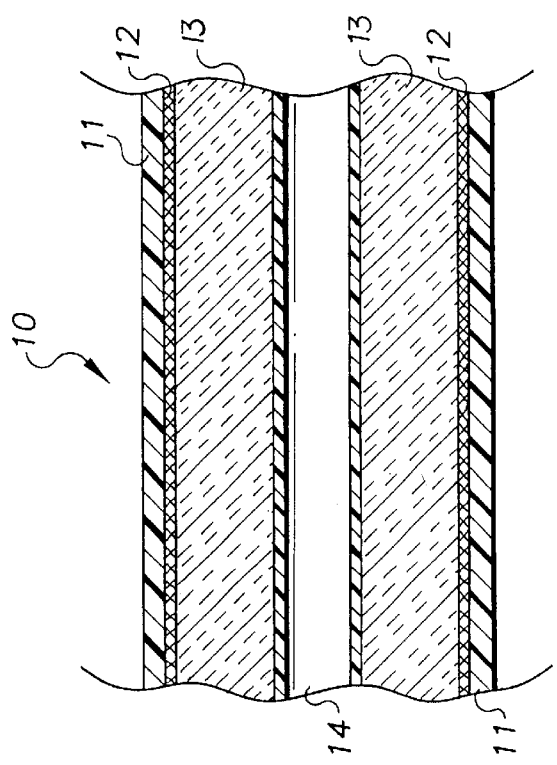
FIG. 2 is an isometric view of a cross-section of an insulated catheter body.

FIG. 2, a preferred embodiment, shows a thermally insulated injection catheter that has an insulated catheter body 10. The insulated catheter body includes a catheter wall 11, a stainless steel mesh layer 12, an insulation layer 13, and a solution tube 14. The catheter wall is typically PEBAX® thermoplastic and is approximately 0.125" in outside diameter. The solution tube transports the therapeutic solution from the syringe, out of the needle, to the target area. The insulation layer and the stainless steel mesh layer limit the transfer of heat between the patient's body and the therapeutic solution, thus maintaining the therapeutic solution in the liquid state as it travels through the insulated catheter body to the target area.

As previously mentioned, the catheter wall 11 is typically PEBAX® resin, and typically 0.118" in outside diameter and 0.091" in inside diameter. It may be constructed of varying durometers or flexibilities from proximal to distal end. The durometer ranges for this type of catheter are typically from 75D to 30D. The catheter may be lined with Teflon, PTFE, ETFE, FEP, polyethylene, polypropylene, or FPA to allow the transition from one diameter to another. The stainless steel mesh layer 12 can be stainless steel braiding or coiling which increase torque transmission and elastic bending properties. The diameter of the stainless steel wires typically used in this construction is 0.0025". The wires may be round or flat. The braiding is typically around 90 picks per inch.

The insulation layer 13 is soft material that has low thermal conductivity, such as, closed or open-celled foams of polyurethane, silicone, polyvinyl alcohol or other thermoplastics or thermosetting plastics. Alternatively, the insulation layer can be made up of windings of flat materials that include these foams, thermoplastics, papers, cellulose, and other thermally insulating materials. The winding pattern and stiffness of these materials are designed to allow the catheter to bend easily so that it can negotiate curves in the patient's vasculature to advance to the target area.

If the therapeutic solution is a reverse-thermal solution, then the insulation layer 13 could be replaced by a high heat capacity fluid or material. A fluid or material whose critical temperature is near the delivery temperature of the reverse-thermal solution keeps the reverse-thermal solution cool by taking heat away from it. The catheter could be filled with this fluid or material at room temperature or it could be precooled before it was used in the catheter lab. This fluid or material (solid, gel or liquid) is protected from the heat of the circulating blood by the insulating properties of the catheter wall.

The solution tube 14 has an outer diameter of typically 0.030" and the inner diameter is sized to fit over the 27 or 28-gauge needle (typically 0.016" inside diameter). The solution tube material can be silicone, urethane, polyethylene, Teflon, PTFE, ETFE, FEP, FPA, polyolefin, PEO or other thermoplastic that is easily extruded. The solution tube carries the therapeutic solution from the syringe to the hollow needle on the distal end of the catheter. The needle is typically constructed of stainless steel but could be insulated with a thermally insulating material (thermoset or thermoplastic) or made of such a material.

Figure 3:
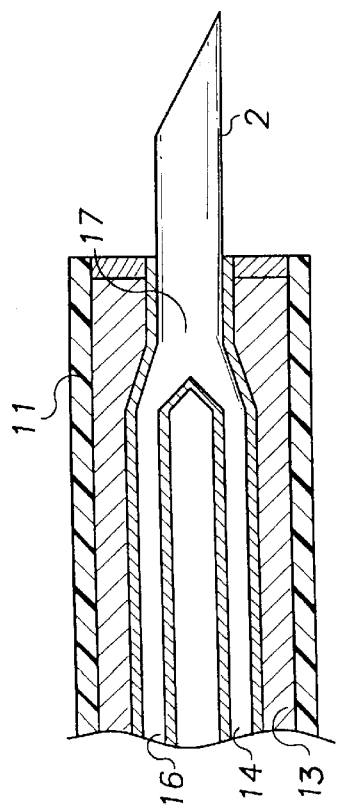
FIG. 3 is an isometric view of a cross-section of a catheter body having a Y-junction.

FIG. 3 shows a second preferred embodiment which includes a second tube, called the alternate tube 16, extending from the distal to the proximal end of the catheter. The alternate tube joins the solution tube at a Y-junction 17 proximate to the hollow needle 2. The surgeon could inject radiopaque contrast through this tube to better visualize locations in the body. This tube could also be used to flush the distal hollow needle or helix of the therapeutic solution after the solution had been injected into the target area. This would ensure that no therapeutic solution resides in the exposed hollow needle thus reducing the small likelihood that the solution could solidify within the device.

When a reverse-thermal solution is used, heated saline could be injected into the alternate tube 16 where the alternate tube is insulated. The heated saline would flush the distal end of the catheter after the reverse-thermal solution had been delivered. Additionally, the heated saline would speed the gelling of the reverse-thermal solution within the target area. In contrast, when a thermal solution is used, cooled saline could be injected into the alternate tube.

Figure 4:
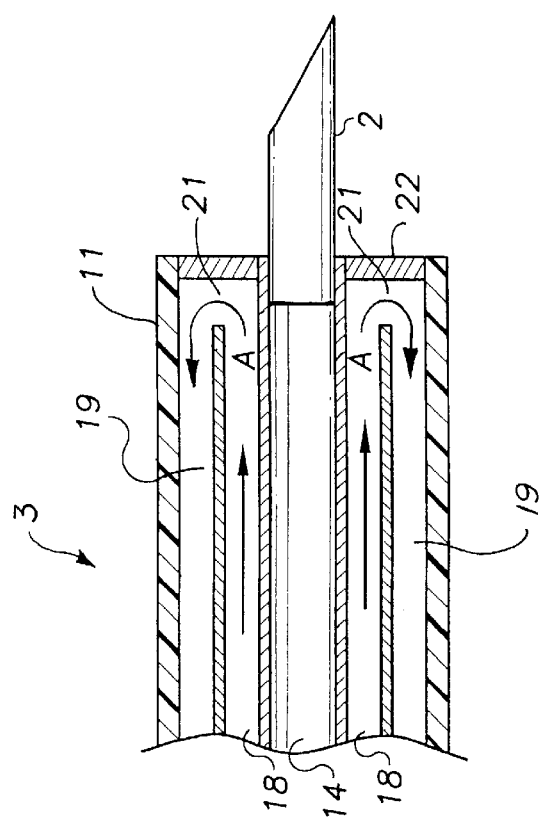
FIG. 4 is an isometric view of a cross-section of a catheter body having an input tube, an output tube, and a solution tube.

FIG. 4 shows a third preferred embodiment which includes a catheter body 3 having a catheter wall 11, a solution tube 14, an input tube 18 and an output tube 19. The input tube surrounds the solution tube and carries a fluid, gas or liquid, along the length of the solution tube through the catheter body toward the distal end of the catheter. The output tube surrounds the input tube and carries the fluid away from the distal end of the catheter. The catheter wall surrounds the output tube.

An opening 21 at the distal end of the catheter connects the input tube 18 and the output tube 19, such that the fluid flows from the proximal end of the catheter to the distal end of the catheter through the input tube. The fluid then flows in the direction of the arrow A into the output tube. Once in the output tube the fluid flows to the proximal end of the catheter. The distal plug 22 prevents fluid from flowing out of the distal end of the catheter into the patient's body.

The fluid is either a heating or a cooling fluid, depending on whether the therapeutic solution is a thermal solution or a reverse-thermal solution. A heating fluid is used if a thermal solution is used, and a cooling fluid is used if a reverse-thermal solution is used. The fluid keeps the therapeutic solution in the liquid state as it travels through the catheter. The fluid convectively cools or heats the therapeutic solution. The term "fluid" is meant in its broad sense, and includes liquids and gases. A compressed gas, such as, nitrogen, carbon dioxide, air, oxygen, helium or other gas can be used as the fluid.

Figure 5:
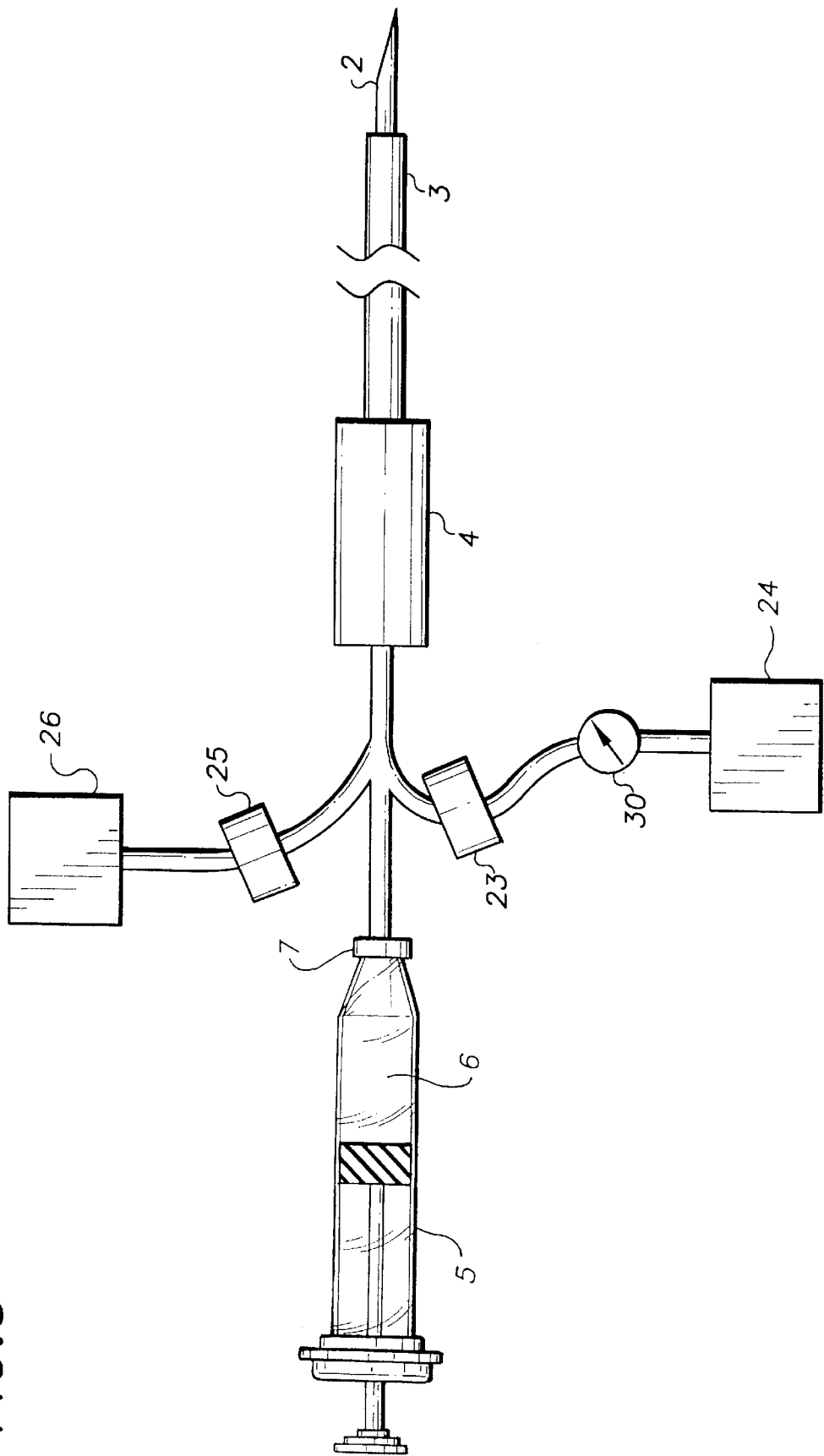
FIG. 5 is an isometric view of an injection catheter having a fluid input and fluid output.

FIG. 5 shows the syringe 5, filled with the therapeutic solution in the liquid state, is connected to the catheter body via a first luer 7. Also connected to the catheter body, via a second luer 23, is a fluid source container 24. Further connected to the catheter body, via a third luer 25, is a fluid output container 26. The therapeutic solution flows from the syringe 5 through the catheter body 4 out of the needle 2 into the target area. The fluid flows from the fluid source container 24 into the input tube, through the opening into the output tube and finally into the fluid output container 26.

A pump 30 draws up the fluid, which can be water, saline, radiopaque contrast material or a gas etc., from the fluid source container and pressurizes it into the proximal end of the input tube of the catheter. Gravity, a pressurized reservoir, hand pressure or other supply of pressurized fluid can also supply the pressure to move the fluid through the catheter.

Figure 6:
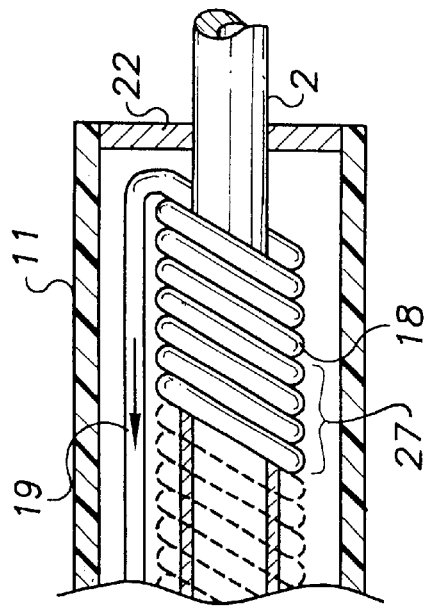
FIG. 6 is an isometric view of a cross-section of a catheter body having an input tube coiled around a solution tube.

FIG. 6 shows the input tube 18 being wrapped in a spiral fashion around the solution tube 14 forming a coil 27. Once the coil reaches the distal end of the catheter, it changes direction 180 degrees and becomes the output tube 19 returning the fluid to the proximal end of the catheter and into the fluid output container.

In another alternative, there could be an input tube and no output tube or distal plug, such that, a cooling fluid flows out the distal end of the catheter into the body. The cooling fluid in this case could be saline. If the cooling fluid is saline, it can continuously empty into the bloodstream without adverse effects on the patient.

The pressure of the fluid carries it out of the catheter and into the fluid output container. When the driving pressure of the fluid is higher than atmospheric pressure, the fluid will flow into the fluid output container, if it is open to the atmosphere. Because of the thermal capacity of the fluid and the volume of fluid flow, the therapeutic solution is kept in the liquid state until it exits the catheter into the target area.

One schooled in the art can envision that the pump can be placed on the output-side of the catheter and could develop a vacuum that would draw the fluid through the catheter instead of pushing it from the input-side. The preferred embodiment also includes controllers to change the rate at which the fluid is pumped, the input temperature of the fluid, and thermocouples tied to temperature readouts which monitor the temperature of the therapeutic solution as it exits the catheter into the target area.

Figure 7:
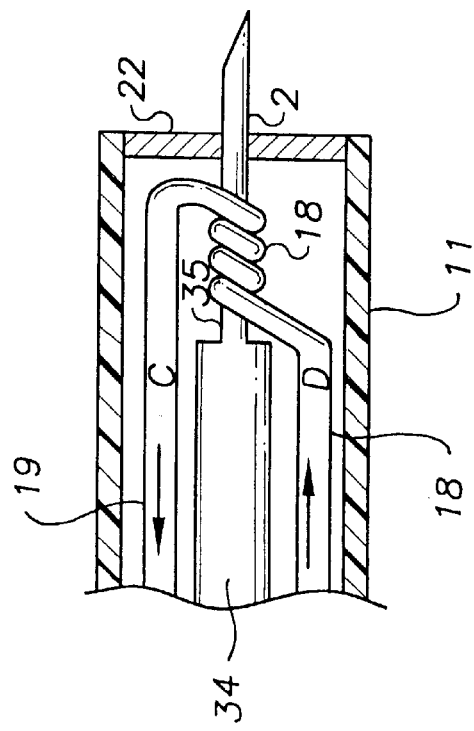
FIG. 7 is an isometric view of a cross-section of a catheter body having a reservoir, a neck section with a coil.

FIG. 7 shows another preferred embodiment, which includes a reservoir 34 filled with the reverse-thermal solution. The reservoir is located at the distal end of the catheter. The reverse-thermal solution is cooled at a neck section 35, which is located proximate to the hollow needle 2 that delivers the reverse-thermal solution. The input tube 18 coils around the neck section and the fluid flows, in the direction of the arrow D, through the input tube cooling the reverse-thermal solution then out the output tube 19, in the direction of the arrow C. The reservoir has a large, constant cross-section. The cooling of the reverse-thermal solution occurs just proximal to the hollow needle 2 liquefying a small amount of reverse-thermal solution. This small amount of reverse-thermal solution is dispensed by the pressure of the reservoir of reverse-thermal solution in the gelled state which acts like a syringe plunger when pressurized at the proximal end of the catheter. Because the large gel reservoir is of a constant cross-sectional area, it can be forced forward under mild pressure (but not through the small opening of the distal needle).

The same configuration could be used wherein the reservoir is filled with the thermal solution. The fluid carried in the input tube heats the neck section thus liquefying the thermal solution in the neck section in order to inject the thermal solution into the target area.

Another embodiment combines cooling fluid and reverse-thermal solution into one tube by injecting reverse-thermal solution "plugs" separated and carried by the cooling fluid. The plugs move down the tube, pushed by the force of injected saline. Once the discrete plugs are lodged in the target area, the saline would be transported away by the body, leaving the reverse-thermal solution plug in place to harden and elute its therapeutic agent over time. The proximal end of the device could have a two-position stopcock that either feeds cool saline or cooled saline carrying discrete plugs, depending on which input source is selected by the stopcock position.

Figure 8:
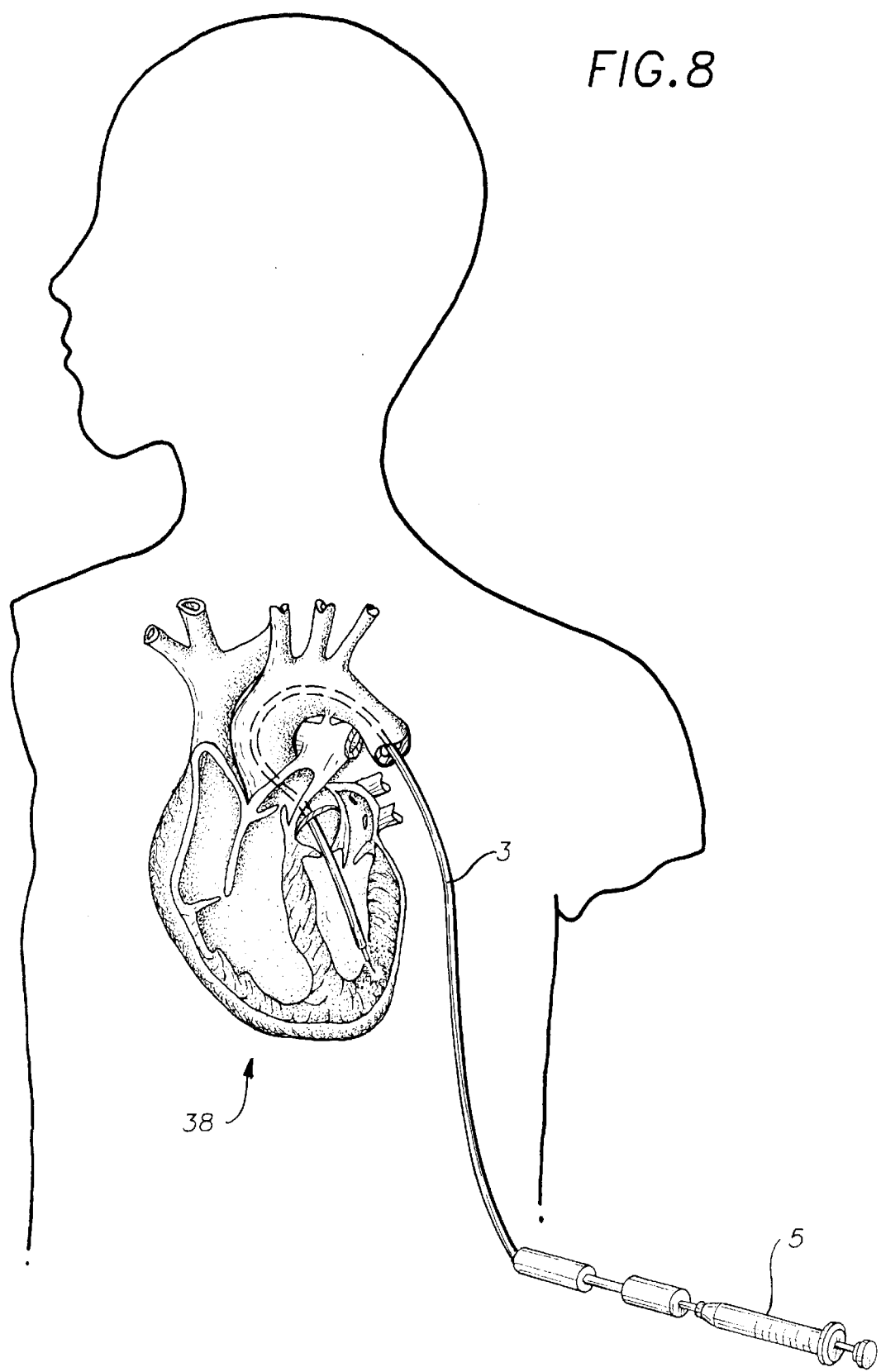
FIG. 8 is an isometric view of an injection catheter in use.
Figure 9:
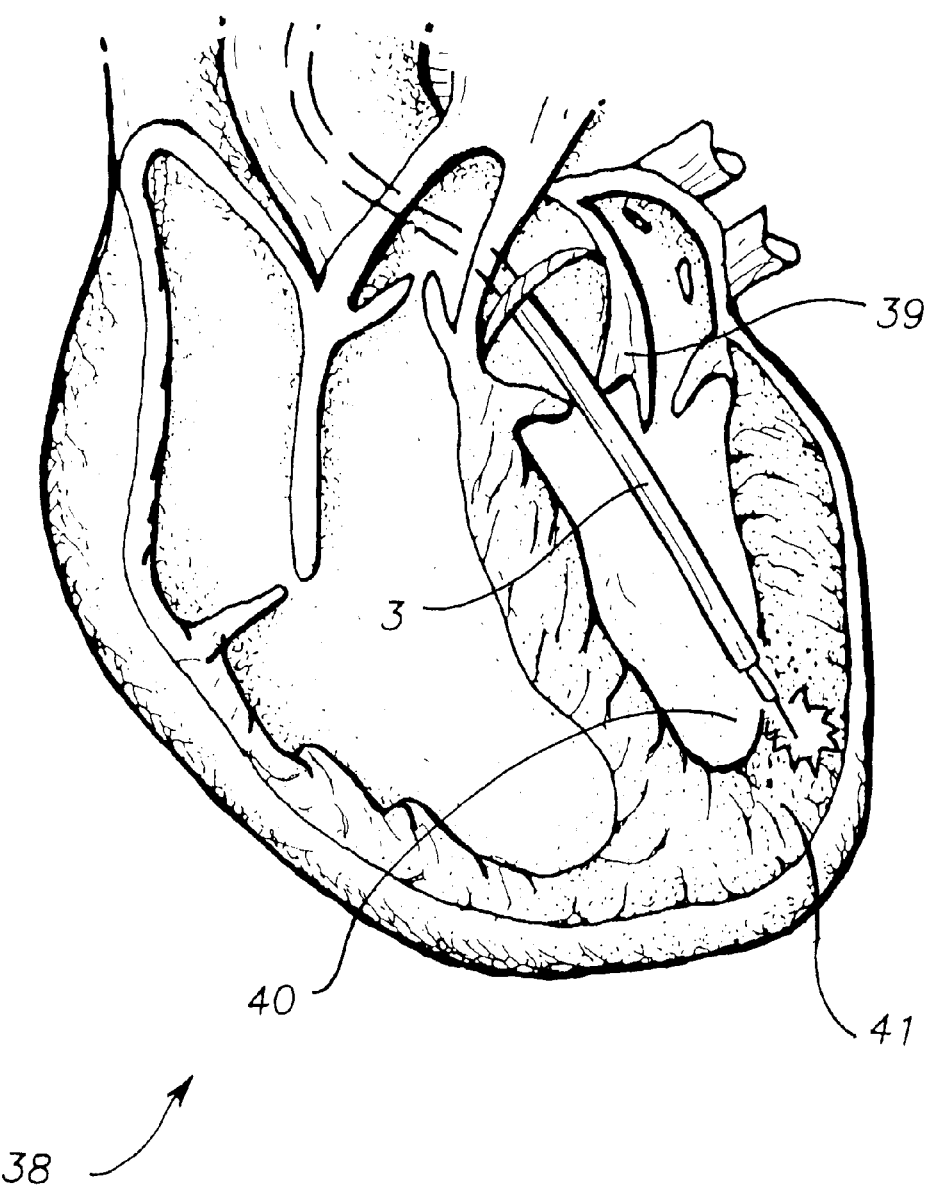
FIG. 9 is an isometric view of the distal end of an injection catheter in use in the heart.

FIGS. 8 and 9 show the catheter in use. The catheter can, for example, deliver the therapeutic solution to the heart 38, where it slowly releases growth factors to treat coronary artery disease over a period of time. In this instance, the injection catheter is routed through the aortic valve 39 to the left ventricle 40 of the heart inside a hollow guide catheter (not shown) specially shaped for this access. Once the distal end of the catheter is carried to the target site, the needle of the catheter is buried in the wall of the myocardium 41. Then the proximal syringe 5 is depressed to dispense the physician-specified amount of therapeutic solution into the myocardium. The injection catheter is removed from the myocardium and repositioned to another site or removed from the patient's body. The injected therapeutic solution then becomes more viscous under the influence of the body temperature of the patient and thus remains in place to elute its therapeutic agents over a period of time. The therapeutic solution for injection into the heart muscle includes antiarrythmia agents, angiogenic growth factors, and other agents having therapeutic effects on heart tissue.

Implantation of therapeutic reverse-thermal solutions with angiogenic agents in concert with a percutaneous transmyocardial revascularization procedure (PTMR) may prove more efficacious than either procedure alone. The localized heating may help start the angiogenic response.

The devices described provide for delivery of therapeutic agents to the myocardium of the left ventricle (retrograde access across the aortic valve), the right atrium and ventricle of the heart (venous access), trans-septally from the right to the left side of the heart, from the coronary sinus into the myocardium, or from the coronary artery vessels into the myocardium of the heart.

There has been recent work on the development and delivery of growth factors, or antigrowth factors to tissues in the human body. These growth factors can be delivered to influence nerves, blood vessels, tissues, bones, cartilage, muscles, or other cells to grow. Gene therapy preparations can also be delivered. These preparations enable cells to produce the therapeutic proteins that encourage the tissues to grow. Anti-growth proteins have been delivered to discourage growth or to kill tissues that are growing abnormally such as anti-restenosis or antitumor drugs, cytotoxic or chemotherapeutic drugs. The cytotoxic or chemotherapeutic drugs include vincristine, vinblastine, cisplatin, methotrexate, and 5-FU. Gene therapies are being developed to enable the body to make the proteins that limit growth or cause cells to die. All of these therapeutic agents can be formulated into therapeutic solutions.

The cooling, heating, or insulating properties of the catheter can also encapsulate the syringe or other pressurized source of therapeutic solution. This would keep the therapeutic solution in its liquid state for a longer period of time. If the therapeutic solution being used were a reverse-thermal solution then it could be insulated it from the heat of the operating room or doctor's body.

There are other pressurizing elements to deliver the therapeutic solution to the target area including power injectors, syringe pumps, roller pumps, compressed-gas-powered syringes, in/deflators, and dosing syringes. All of these could be used with the devices and methods described above because they can be joined to the input tube at the luer connector at the proximal end of the catheter.

Features could be added to the catheter to control the depth that the needle tip penetrates the tissue at the target area. Another possible feature is to measure the amount of therapeutic solution that is delivered at the distal end of the catheter.

Another embodiment uses electrical, magnetic, radiofrequency, ultrasonic, laser, ultraviolet, or other energy source at the distal end of the catheter to speed the gelling of reverse-thermal solutions after they have been delivered, and the needle flushed of its contents with saline. This is particularly useful in tumor ablation procedures. The additional heat generated by the energy source kills some of the aberrant tumor cells and the delivered reverse-thermal solution continues killing the tumor cells after the acute treatment provided by the energy source.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A catheter system for injecting a therapeutic agent into a target site within the body of a patient, wherein the therapeutic agent exhibits differing viscosity at different temperatures, said catheter system comprising:
   a catheter having a distal end adapted for inserting into the body and a proximal end adapted for receiving fluid from one or more reservoirs, said catheter comprising:
      a first lumen extending from the proximal end of the catheter to the distal end of the catheter and communication to the exterior of the catheter near the distal end;
      an outer layer and an insulating layer disposed within the outer layer, said insulating layer surrounding the first lumen; and
      a layer located between the insulation layer and the catheter wall.

2. The catheter system of claim 1 wherein the insulating layer comprises:
   a fluid having a high heat capacity.

3. The catheter system of claim 1 wherein the insulating layer comprises foam.

4. The catheter system of claim 1 wherein the insulating layer comprises a thermoplastic material.

5. The catheter system of claim 1 wherein the insulating layer comprises a thermosetting material.

6. The catheter system of claim 1 wherein the insulating layer comprises polyurethane foam.

7. The catheter system of claim 1 wherein the insulating layer comprises silicone foam.

8. The catheter system of claim 1 wherein the insulating layer comprises polyvinyl alcohol foam.

9. The catheter system of claim 1 wherein the insulating layer comprises paper.

10. The catheter system of claim 1 wherein the insulating layer comprises cellulose.

11. The catheter system of claim 1 wherein the insulating layer comprises windings of material having a high heat capacity.

12. The catheter system of claim 1 wherein the insulating layer comprises windings of material chosen from the group of polyurethane, silicone, polyvinyl alcohol, polyurethane foam, silicone foam, polyvinyl alcohol foam, paper, or cellulose.

13. The catheter system of claim 1 further comprising:
   a reservoir of therapeutic material having a first viscosity at body temperature and a second viscosity at room temperature; and
   means for injecting the therapeutic material from the reservoir into the first lumen.

14. The catheter system of claim 13 wherein the therapeutic material Comprises a thermally sensitive gelling material.

15. The catheter system of claim 13 wherein the therapeutic material comprises a reverse-thermal gel.

16. The catheter system of claim 13 wherein the therapeutic material comprises a thermal gel.

17. The catheter system of claim 13 wherein the therapeutic material comprises a thermally sensitive gelling material.

18. The catheter system of claim 13 wherein the layer located between the insulation layer and The catheter is comprised of stainless steel mesh.

19. The catheter system of claim 1 wherein:
   the insulating layer comprises a second lumen located proximate the first lumen, said lumen extending from the proximal end of the catheter toward the distal end of the catheter, said lumen being adapted to receive a fluid from the proximal end of the catheter.

20. The catheter system of claim 19 further comprising:
   a reservoir of the thermally insulating fluid; and
   means for injecting the thermally insulating fluid from the reservoir into the second lumen.

21. The catheter system of claim 20 wherein the second lumen is coaxially disposed about the first lumen.

22. The catheter system of claim 20 wherein the second lumen is open to the exterior of the catheter near the distal end of the catheter.

23. The catheter system of claim 20 further comprising a third lumen in fluid communication with the second lumen near the distal end of the second lumen, said third lumen extending proximally to the proximal end of the catheter.

24. The catheter system of claim 23 wherein the third lumen is coaxially disposed about the first lumen.

25. The catheter system of claim 19 wherein the thermally insulating fluid reservoir is filled with saline maintained a temperature different than body temperature.

26. The catheter system of claim 19 wherein the second lumen is coaxially disposed about the first lumen.

27. The catheter system of claim 19 wherein the second lumen is open to the exterior of the catheter near the distal end of the catheter.

28. A catheter system for injecting a therapeutic agent into a target site within the body of a patient, wherein the therapeutic agent is a reverse-thermal gel, said catheter system comprising:
   a catheter having a distal end adapted for inserting into the body and a proximal end adapted for receiving fluid from one or more reservoirs, said catheter comprising:
      a first lumen extending from the proximal end of the catheter to the distal end of the catheter and communication to the exterior of the catheter near the distal end;
      an outer layer and an insulating layer disposed within the outer layer, said insulating layer surrounding the first lumen; and
      a layer located between the insulation layer and the catheter wall; and
      a reservoir of therapeutic agent comprising a reverse thermal gel, said reservoir adapted for fluid communication with the first lumen.

29. The catheter system of claim 28 wherein the insulating layer comprises foam.

30. The catheter system of claim 28 wherein the insulating layer comprises a thermoplastic material.

31. The catheter system of claim 28 wherein the insulating layer comprises a thermosetting material.

32. The catheter system of claim 28 wherein the insulating layer comprises polyurethane foam.

33. The catheter system of claim 28 wherein the insulating layer comprises silicone foam.

34. The catheter system of claim 28 wherein the insulating layer comprises polyvinyl alcohol foam.

35. The catheter system of claim 28 wherein the insulating layer comprises paper.

36. The catheter system of claim 28 wherein the insulating layer comprises cellulose.

37. The catheter system of claim 28 wherein the insulating layer comprises windings of material having a high heat capacity.

38. The catheter system of claim 28 wherein the insulating layer comprises windings of material chosen from the group of polyurethane, silicone, polyvinyl alcohol, polyurethane foam, silicone foam, polyvinyl alcohol foam, paper, or cellulose.

* * * * *